US012751969B2

(12) United States Patent
Qureshi

(10) Patent No.: US 12,751,969 B2
(45) Date of Patent: Oct. 6, 2026

(54) INTRAVENOUS PHYSIOLOGICAL SOLUTION TO OPTIMIZE FLUID THERAPY IN PATIENTS

(71) Applicant: Adnan I. Qureshi, Columbia, MO (US)

(72) Inventor: Adnan I. Qureshi, Columbia, MO (US)

( * ) Notice: Subject to any disclaimer, the term of this patent is extended or adjusted under 35 U.S.C. 154(b) by 210 days.

(21) Appl. No.: 18/734,760

(22) Filed: Jun. 5, 2024

(65) Prior Publication Data

US 2024/0316095 A1 Sep. 26, 2024

Related U.S. Application Data

(63) Continuation-in-part of application No. 17/525,914, filed on Nov. 14, 2021, now Pat. No. 12,029,756.

(51) Int. Cl.

| | |
|---|---|
| ***A61K 33/14*** | (2006.01) |
| ***A61K 9/00*** | (2006.01) |
| ***A61K 33/00*** | (2006.01) |

(52) U.S. Cl.

CPC ............ *A61K 33/14* (2013.01); *A61K 9/0019* (2013.01); *A61K 33/00* (2013.01)

(58) Field of Classification Search

None

See application file for complete search history.

(56) References Cited

PUBLICATIONS

Finfer et al., Intravenous fluid therapy in critically ill adults, Nature Review, Nephrology vol. 14, Sep. 2018 (Year: 2018).*

* cited by examiner

*Primary Examiner* — Anna R Falkowitz

*Assistant Examiner* — Edwin Coleman Mitchell

(74) *Attorney, Agent, or Firm* — Patent 360; Barry Choobin

(57) ABSTRACT

An intravenous fluid composition includes sodium chloride and sodium acetate that can provide appropriate sodium load and osmolality, with chloride concentration and pH mimicking normal values in human blood.

3 Claims, No Drawings

INTRAVENOUS PHYSIOLOGICAL SOLUTION TO OPTIMIZE FLUID THERAPY IN PATIENTS

CROSS-REFERENCE TO RELATED APPLICATIONS

This applicant is a continuation-in-part of a U.S. patent application Ser. No. 17/525,914 filed on Nov. 14, 2021, which is incorporated herein by reference in its entirety.

FIELD OF THE INVENTION

The present invention relates to an intravenous fluid composition, and more particularly, the present invention relates to intravenous solution for maintaining fluid balance in the body.

BACKGROUND

Several studies have demonstrated an association between hyperchloremia and the occurrence of acute kidney injury (AKI) and short- and long-term mortality in patients admitted to critical care units. Approximately 18% of patients with stroke have a new onset hyperchloremia. One study demonstrated that hyperchloremia after ischemic stroke was associated with increased rates of AKI and longer hospital length of stay. More recently, higher rates of in-hospital mortality were observed in patients with intracerebral hemorrhage (ICH) who developed moderate hyperchloremia during treatment with continuous intravenous (IV) infusion 3% hypertonic saline. Perioperative hyperchloremia was independently related to an increased incidence of AKI after craniotomy for ICH. New-onset hyperchloremia and every 5 mmol/L increments in serum chloride were both associated with increased odds of 30-day mortality and 6-month poor outcome in patients with either ischemic stroke or ICH.

Normal saline is the solution most widely employed in medical and pediatric care, as well as in hematology and transfusion medicine. There are commercially available balanced crystalloids with low chloride content for intravenous administration. These included normal saline, succinylated gelatin (Gelofusine: chloride 120 mmol/L, sodium 154 mmol/L), albumin in sodium chloride (Albumex 4: chloride 128 mmol/L, sodium 140 mmol/L), lactated Ringer's solution (Na 130 mmol/L, Chloride 109 mmol/L) and Plasma-Lyte A (Sodium 140 mmol/L, Chloride 98 mmol/L). A meta-analysis of 21 studies involving 6253 patients found that high-chloride fluids were associated with a significantly higher risk of AKI, hyperchloremia, metabolic acidosis, blood transfusion volume, and mechanical ventilation time. However, low chloride fluids did not reduce mortality. The Isotonic Solutions and Major Adverse Renal Events Trial (SMART) compared normal saline with balanced crystalloids (lactated Ringer's solution or Plasma-Lyte A) in 15,802 critically ill adults. The primary outcome of a composite of major renal AE within 30 days, death from any cause, new renal-replacement therapy, or persistent renal dysfunction was significantly higher in patients who received normal saline (15.4% versus 14.3%). Paradoxically, the primary outcome was lower in the saline group (14% versus 15%) in patients with traumatic brain injury and higher in patients without traumatic brain injury (15.5% versus 14.3%) suggesting that the results of these trials should not be extrapolated to patients with intracranial pathology. Some of the most commonly used 'balanced' solutions (like lactated Ringer's solution) are neither isotonic nor precisely balanced. With an osmolality of 273 mOsm/L and a measured osmolality of 254 mOsm/L, infused lactated Ringer's solution leads to a small decrease in plasma osmolality. Slightly hypotonic infusion fluids may increase brain water content worsening cerebral edema.

The commercially available normal saline (0.9% sodium chloride) has a pH of 5.5. The salt results from the reaction of a strong acid with a strong base, the pH will be 7. This is the case, for example, of NaCl that results from the reaction of HCl and NaOH. Pure distilled water has a pH of 7 at 25° C. However, in contact with the atmosphere, carbon dioxide is absorbed, and the pH of normal saline or distilled water is reduced to approximately 5.65. The pH is further reduced due to the polyvinyl chloride bags that are used to store normal saline.

It is evident that the known IV fluids have high chloride content which is undesirable. Also, decreasing the chloride content decreases the sodium content proportionally resulting in the fluid that cannot maintain the desired osmotic gradient. A need is appreciated for an IV fluid that can maintain the osmotic gradient within desired levels and prevent cerebral edema and high intracranial pressure.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

It is therefore the principal object of the present invention directed to an intravenous fluid composition that has low chloride but has relatively high sodium content.

It is another object of the present invention that the intravenous fluid composition does not cause cerebral edema.

It is still another object of the present invention that the intravenous fluid composition does not result in high intracranial pressure.

It is yet another object of the present invention that the intravenous fluid composition can be used in the treatment of high intracranial pressure and cerebral edema.

In one aspect, disclosed is an intravenous fluid composition comprising sodium chloride, sodium acetate, and optionally potassium acetate, wherein the intravenous fluid composition has an osmolality close to serum osmolality of 295 mOsm/L.

In one aspect, 6000 mg of sodium chloride, and 4000 mg of sodium acetate, with or without 300 mg potassium acetate in 1 Liter of distilled water are mixed to obtain the disclosed intravenous fluid composition. The intravenous fluid composition contains sodium chloride 205 mmol/L and sodium acetate 97.5 mmol/L with potassium acetate 6 mmol/L with a theoretical osmolality of 302.5 mOsm/L to 308.5 mOsm/L and a pH of approximately 7.

In one aspect, disclosed is a method of preparing the disclosed intravenous fluid composition including the steps of mixing sodium chloride and sodium acetate in distilled water at 40-60° C. to obtain a solution; filling the solution in a bag; and cooling down the solution to room temperature in the bag.

DETAILED DESCRIPTION

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word “exemplary” is used herein to mean “serving as an example, instance, or illustration.” Any embodiment described herein as “exemplary” is not necessarily to be construed as preferred or advantageous over other embodiments. Likewise, the term “embodiments of the present invention” does not require that all embodiments of the invention include the discussed feature, advantage, or mode of operation.

The terminology used herein is for the purpose of describing particular embodiments only and is not intended to be limiting of embodiments of the invention. As used herein, the singular forms “a”, “an” and “the” are intended to include the plural forms as well, unless the context clearly indicates otherwise. It will be further understood that the terms “comprises”, “comprising,”, “includes” and/or “including”, when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

In one aspect, disclosed is a saline intravenous fluid composition that includes sodium chloride and sodium acetate in pre-determined concentration in the distilled water. The disclosed intravenous fluid composition includes high sodium content and comparatively low chloride content thus can maintain desired osmotic gradient. The desired osmotic gradient can be such that to pull water from the brain through the blood brain barrier into the serum to prevent and treat cerebral edema and high intracranial pressure.

Also, disclosed is a method of preparing the intravenous fluid composition by mixing sodium chloride and sodium acetate in distilled water at 40-60° C., and more preferably at 40° C. to obtain a solution. The solution can be filled in packaging bags while hot and allowed to cool to room temperature in the packaging bag. The resulting intravenous fluid composition can have the pH of about 7 and the pH can be maintained for a long period.

Experiment 1

A study was conducted in which the data of patients with spontaneous ICH within 4.5 hours of symptom onset were analyzed. Patients with an increased serum chloride (110 mmol/L or greater) at either baseline, or 24, 48, or 72 hours after randomization were identified. Among the total of 1000 patients analyzed, one and two or more occurrences of hyperchloremia within 72 hours were seen in 114 patients and 154 patients, respectively. Compared with patients without hyperchloremia, patients with one occurrence of hyperchloremia (odds ratio [OR] 2.5, 95% confidence interval [CI] 1.1-5.6), and those with two or more occurrences (OR 2.6, 95% CI 1.3-5.0) at significantly higher odds of death within 90 days after adjustment for age, race/ethnicity, National Institutes of Health Stroke Scale (NIHSS) score strata, hematoma volume, presence or absence of intraventricular hemorrhage, cigarette smoking, and previous stroke. Compared with patients without hyperchloremia, patients with two or more occurrences (OR 3.5, 95% CI 2.1-5.7) at significantly higher odds of death or disability at 90 days.

Experiment 2

In another study was analyzed the data from Albumin in Acute Ischemic Stroke (ALIAS) Part 1 and 2 trials recruited patients with acute ischemic stroke within 5 hours of symptom onset. Patients with an increased serum chloride (110 mmol/L or greater) at either baseline, or 24, or 48 hours after randomization were identified. We further graded hyperchloremia into one occurrence or two or more occurrences within the first 48 hours. Among the total of 1275 patients analyzed, one and two or more occurrences of hyperchloremia within 48 hours were seen in 191 patients and 108 patients, respectively. Compared with patients without hyperchloremia, patients with two or more occurrences of hyperchloremia (OR 3.0, 95% CI 1.8-5.0) at significantly higher odds of non-favorable outcomes within 90 days after adjustment for age, NIHSS score strata, initial systolic blood pressure, and treatment group (albumin or placebo). Compared with patients without hyperchloremia, patients with two or more occurrences of hyperchloremia at non-significantly higher odds of death within 90 days after adjusting for potential confounders. Patients with one occurrence of hyperchloremia were not at higher odds for non-favorable outcomes at 90 days.

Experiment 3: Preparation of the Disclosed Intravenous Fluid Composition

1 L of distilled water was heated up to 40° C. under a pressure of about 25 atmospheres. Thereafter, 6000 mg of sodium chloride, 4000 mg of sodium acetate, and optionally 300 mg potassium acetate were mixed, while maintaining the pressure, in the water to obtain a solution. The solution while hot was filled in a packaging bag. The solution in the packaging bag was allowed to cool to room temperature. The solution contains sodium chloride 205 mmol, sodium acetate 97.5 mmol, and potassium acetate 6 mmol with a theoretical osmolality of 302.5 mOsm/L to 308.5 mOsm/L and PH of approximately 7.

TABLE 1

Comparison of disclosed fluid composition with existing saline compositions (mmol/L).

| | Na | K | Mg | Ca | Chloride | Acetate | Gluconate | Lactate | Malate |
|---|---|---|---|---|---|---|---|---|---|
| Plasma | 136-145 | 3.5-5.0 | 0.8-1.0 | 2.2-2.6 | 98-106 | Nil | Nil | Nil | Nil |
| Sodium chloride (0.9%) | 154 | Nil | Nil | Nil | 154 | Nil | Nil | Nil | Nil |
| Compound sodium Lactate (lactate buffered) | 129 | 5 | Nil | 2 | 109 | Nil | Nil | 29 | Nil |
| Ringer's lactate (lactate buffered) | 130 | 4 | Nil | 3 | 109 | Nil | Nil | 28 | Nil |
| Ionosteril ® (acetate buffered solution) | 137 | 4 | 1.25 | 1.65 | 110 | 36.8 | Nil | Nil | Nil |
| Sterofundin ISO ® (acetate and malate buffered) | 145 | 4 | 1 | 2.5 | 127 | 24 | Nil | Nil | 5 |
| Plasma-Lyte 148 ® (acetate and gluconate buffered) | 140 | 5 | 1.5 | Nil | 98-106 | 27 | 23 | Nil | Nil |
| Disclosed composition | 132.3-151.8 | 0-3.6 | Nil | Nil | 77.5-115.5 | 27.7-55.3 | Nil | Nil | Nil |

TABLE 2

Comparison of Osmolality and pH of proposed fluid with existing fluids.

| | Theoretical osmolarity (mOsm/kg) | Actual or measured osmolality (mOsm/kg) | pH |
|---|---|---|---|
| Plasma | 291 | 287 | 7.35-7.45 |
| Sodium chloride (0.9%) | 308 | 286 | 4.5-7 |
| Compound sodium Lactate (lactate buffered) | 278 | 278 | 5-7 |
| Ringer's lactate (lactate buffered) | 278 | 256 | 5-7 |
| lonosteril ® (acetate buffered solution) | 291 | 20 | 6.9-7.9 |
| Sterofundin ISO ® (acetate and malate buffered) | 309 | Not stated | 5.1-5.9 |
| Plasma-Lyte 148 ® (acetate and gluconate buffered) | 295 | 271[b] | 7.4[c] |
| Disclosed composition | 269.7-308.5 | Not measured | 7.0-7.4 |

In one exemplary embodiment, disclosed is an intravenous fluid composition comprising 4500-7000 mg of sodium chloride, and 2250-4500 mg of sodium acetate, and 300 mg of potassium acetate in 1 Liter of distilled water, wherein the solution has a calculated osmolality of 300-310 mOsm/L.

In a preferred embodiment, the disclosed intravenous fluid composition can be prepared from 6000 mg of sodium chloride, and 3000 mg of sodium acetate in 1 Liter of distilled water. The solution contains sodium chloride 205 mmol and sodium acetate 71.5 mmol with a calculated osmolality of 276 mOsm/L and pH of approximately 7.

In a preferred embodiment, the disclosed intravenous fluid composition can be prepared from 6000 mg of sodium chloride, and 4000 mg of sodium acetate, with or without 300 mg potassium acetate in 1 Liter of distilled water. The solution contains sodium chloride 205 mmol and sodium acetate 97.5 mmol with potassium acetate 6 mmol with a calculated osmolality of 302.5 mOsm/L to 308.5 mOsm/L and pH of approximately 7.

In a preferred embodiment, the disclosed intravenous fluid composition can be prepared from 6750 mg of sodium chloride, and 2250 mg of sodium acetate, with or without 300 mg potassium acetate in 1 Liter of distilled water. The solution contains sodium chloride 231 mmol, sodium acetate 54.9 mmol, and potassium acetate 6 mmol with a calculated osmolality of 292 mOsm/L and pH of approximately 7.

In a preferred embodiment, the disclosed intravenous fluid composition can be prepared from 6000-7000 mg of sodium chloride, and 3500-4000 mg of sodium acetate, and 300 mg of potassium acetate in 1 Liter of distilled water to increase the calculated osmolality of greater than 310 mOsm/L.

In one exemplary embodiment, the disclosed composition can be prepared from sodium chloride and a second salt selected from sodium diacetate or sodium bicarbonate.

In another embodiment, disclosed composition can be formed using a mixture of sodium chloride, sodium acetate, and potassium acetate that comprises of 6750 mg of sodium chloride, and 2250 mg of sodium acetate, with or without 300 mg potassium acetate in 1 Liter of distilled water. The solution contains sodium chloride 231 mmol, sodium acetate 54.9 mmol, and potassium acetate 6 mmol with a calculated osmolality of 292 mOsm/L and pH of approximately 7. However, the potassium acetate can be optional and the composition without potassium acetate can have the calculated osmolality of 286 mOsm/L.

In another embodiment, disclosed composition can be formed using a mixture of sodium chloride, sodium acetate, and potassium acetate that comprises of 4500 mg of sodium chloride, and 4500 mg of sodium acetate, with or without 300 mg potassium acetate in 1 Liter of distilled water. The solution contains sodium chloride 153.8 mmol, sodium acetate 109.7 mmol, and potassium acetate 6 mmol with a calculated osmolality of 269.5 mOsm/L and pH of approximately 7.

It is to be noted that the calculated osmolality is based on assumption that each mmol of sodium, chloride and acetate provide one mOsm/L. The calculated osmolality assumes that each mmol of sum of all osmotically active particles in a solution. For example, 6000 mg of sodium chloride (molar mass=58.4 g/mol) results in 102.5 mmol but sodium chloride will dissolve releasing two particles in water (sodium and chloride) that will contribute independently to osmotic pressure. Therefore, each mmol/L of sodium chloride has an osmolality of 2 mOsm/L. Thus 6000 mg of sodium chloride in 1 L water has an osmolality of 205 mOsm/L. Similarly, 3000 mg of sodium acetate (molar mass=82.03 g/mol) results in 36.5 mmol but sodium acetate will dissolve releasing two particles in water (sodium and acetate) that will contribute independently to osmotic pressure. Therefore, each mmol/L of sodium acetate has an osmolality of 2 mOsm/L. Thus 3000 mg of sodium acetate in 1 L water has an osmolality of 73 mOsm/L. Similarly, 300 mg of potassium acetate (molar mass=98.14 g/mol) results in 3.05 mmol but potassium acetate will dissolve releasing two particles in water (potassium and acetate) that will contribute independently to osmotic pressure. Therefore, each mmol/L of potassium acetate has an osmolality of 2 mOsm/L. Thus 300 mg of potassium acetate in 1 L water has an osmolality of 6.1 mOsm/L.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. An intravenous fluid solution consists of 6750 mg of sodium chloride, 2250 mg of sodium acetate, and 300 mg potassium acetate in 1 Liter of distilled water, wherein the intravenous fluid solution has a calculated osmolality of 292 mOsm/kg.

2. An intravenous fluid solution consists of 6750 mg of sodium chloride and 2250 mg of sodium acetate in 1 Liter of distilled water, wherein the intravenous fluid solution has a calculated osmolality of 286 mOsm/kg.

3. A method for preparing a pharmacological solution for intravenous administration, the method consisting of the steps:

mixing 6750 mg of sodium chloride, 2250 mg of sodium acetate, and 300 mg potassium acetate in 1 Liter of distilled water at 40-60° C. to obtain a solution;

filling the solution, while at 40-60° C., in a packaging bag; and cooling down the solution to room temperature in the packaging bag.

* * * * *